(12) United States Patent
Sarwar et al.

(10) Patent No.: US 8,936,765 B2
(45) Date of Patent: Jan. 20, 2015

(54) AUTOMATIC ANALYZER

(75) Inventors: Shahed Sarwar, Hitachinaka (JP); Kazuhiro Tanaka, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 204 days.

(21) Appl. No.: 13/147,206

(22) PCT Filed: Feb. 12, 2010

(86) PCT No.: PCT/JP2010/052093
§ 371 (c)(1),
(2), (4) Date: Sep. 9, 2011

(87) PCT Pub. No.: WO2010/093022
PCT Pub. Date: Aug. 19, 2010

(65) Prior Publication Data
US 2012/0121465 A1      May 17, 2012

(30) Foreign Application Priority Data

Feb. 12, 2009   (JP) .................................. 2009-030464

(51) Int. Cl.
*G01F 23/24* (2006.01)
*G01F 23/26* (2006.01)
*G01N 35/10* (2006.01)

(52) U.S. Cl.
CPC ........ *G01N 35/1011* (2013.01); *G01N 35/1009* (2013.01); *G01F 23/263* (2013.01); *G01F 23/266* (2013.01); *G01N 2035/1025* (2013.01)
USPC ........... 422/517; 422/501; 422/106; 436/180; 73/864.01; 73/304 C; 324/662; 324/691; 324/686

(58) Field of Classification Search
None
See application file for complete search history.

(56) References Cited

U.S. PATENT DOCUMENTS 4,970,468 A *  11/1990  Ishizawa et al. ............... 324/662
6,319,718 B1  11/2001  Matsubara et al.

FOREIGN PATENT DOCUMENTS

| DE | 689 19 167 T2 | 5/1995 |
|---|---|---|
| JP | 63-259420 A | 12/1988 |
| JP | 2-59619 A | 2/1990 |
| JP | 06-148207 A | 5/1994 |
| JP | 09-127132 A | 5/1997 |
| JP | 09127132 * | 5/1997 |
| JP | 2001-4642 A | 1/2001 |
| JP | 2003-114239 A | 4/2003 |
| JP | 2008-089609 A | 4/2008 |
| JP | 2008-249726 A | 10/2008 |
| JP | 2008-298755 A | 12/2008 |

* cited by examiner

*Primary Examiner* — P. Kathryn Wright
(74) *Attorney, Agent, or Firm* — Mattingly & Malur, PC

(57) ABSTRACT

An automatic analyzer having a reaction vessel in which an analyte is caused to react with a reagent; a probe for suctioning the reacted analyte from the reaction vessel; an analyzer unit for analyzing the reacted analyte; a transfer channel for transferring the reacted analyte suctioned by the probe to the analyzer unit 6; and a liquid-surface detector, connected to the reaction vessel and the probe via signal lines 1*a* and a pair of signal lines 4*a* and 4*b*, respectively, for detecting the electrical characteristics between the probe and the reaction vessel. A switch is located between the signal lines 4*a* and 4*b* that connect the liquid-surface detector to the probe, so that the switch can connect or disconnect the signal line 4*a* to/from the signal line 4*b*.

2 Claims, 5 Drawing Sheets

US 8,936,765 B2

AUTOMATIC ANALYZER

TECHNICAL FIELD

The present invention relates to automatic analyzers that qualitatively and quantitatively analyze biological samples such as blood serum and urine.

BACKGROUND ART

Automatic analyzers are used to measure the properties of analytes (e.g., biological samples, such as blood serum and urine, or analyte-reagent mixtures), thereby performing analysis of the analytes.

Such an automatic analyzer typically uses a probe to suction an analyte (or an analyte-reagent mixture) so that the analyte can be transferred to its analyzer unit. In such a case, it is necessary to immerse the lower end of the probe as shallowly into the analyte as possible, so as to prevent the analyte from being attached to the outer surface of the probe and then mixed with another analyte (in other words, to prevent cross-contamination). For this reason, what is needed is detection of the liquid surface level of the analyte relative to the probe.

A known conventional liquid-surface detection technique involves the use of a probe both as an electrode and as an electrically active component. The probe is used for the detection of the capacitance between the probe and a grounded reaction vessel (i.e., the analyte therein, which is also grounded), and monitoring changes in the capacitance allows detection of the liquid surface level of the analyte relative to the probe (see Patent Document 1).

PRIOR ART DOCUMENT

Patent Document

Patent Document 1: JP-2001-004642-A

SUMMARY OF THE INVENTION

Problems to be Solved by the Invention

With the drastic increase in the analysis accuracy of automatic analyzers, analysis results are now more susceptible to various subtler factors.

As for the above-described conventional technique, which may require a channel to be provided between the probe and the analyzer unit for the transfer of an analyte, it may be difficult or impossible to obtain accurate analysis results. This is due to the possibility that electrical fluctuations (e.g., electric signals and associated electric noise) which arise from the liquid-surface detection circuit may adversely affect the analyzer unit through the probe and through the analyte flowing inside the channel.

The present invention has been made to address the above issue, and its object is to provide an automatic analyzer that is capable of preventing electric signals and noise from affecting analysis results.

Means for Solving the Problems

To achieve the above object, an automatic analyzer according to the invention comprises the following components: a reaction vessel in which an analyte is caused to react with a reagent; a probe for suctioning the reacted analyte from the reaction vessel; an analyzer unit for analyzing the reacted analyte; a transfer channel for transferring the reacted analyte suctioned by the probe to the analyzer unit; a detector, connected to the probe and the reaction vessel via signal lines, respectively, for detecting electrical characteristics between the reaction vessel and the probe; and blocking means for preventing electrical fluctuations that arise from the detector from reaching the analyzer unit.

Effect of the Invention

The invention prevents analysis results from being affected by electric signals and noise.

MODE FOR CARRYING OUT THE INVENTION

An embodiment of the present invention will now be described with reference to the accompanying drawings.

Figure 1:
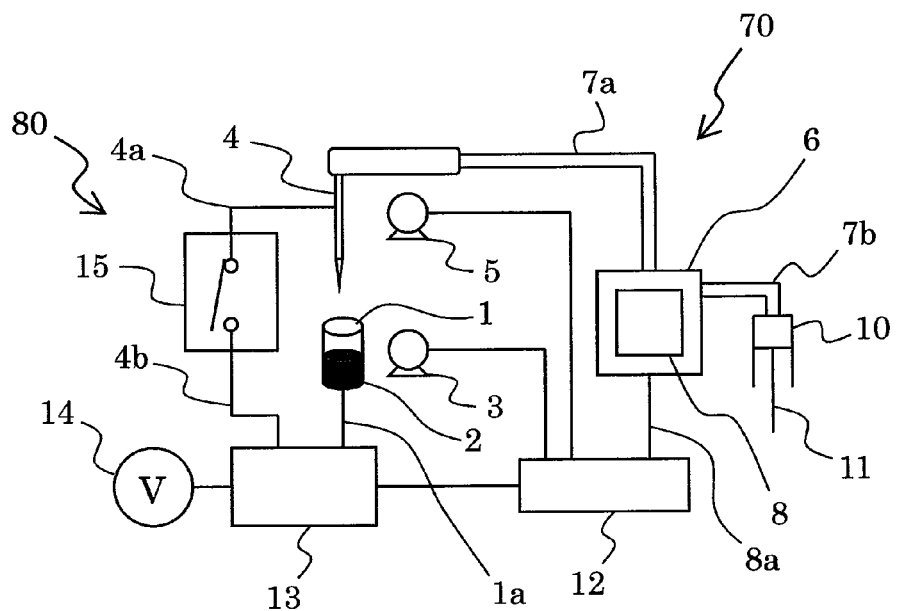
FIG. 1 is a schematic illustrating the overall configuration of an automatic analyzer according to an embodiment of the invention.

FIG. 1 is a schematic illustrating the overall configuration of an automatic analyzer according to the embodiment.

The automatic analyzer of FIG. 1 includes the following components: a reaction vessel 1 into which an analyte-reagent mixture 2 (hereinafter simply called the analyte 2) is injected; an analyzer unit 6 for analyzing the analyte 2; a probe 4 for suctioning the analyte 2 from the reaction vessel 1; a transfer unit 70 for transferring the suctioned analyte 2 to the analyzer unit 6; a liquid-surface detector unit 80 for detecting the liquid surface level of the analyte 2 relative to the probe 4; and a controller 12 for controlling the entire operation of the automatic analyzer.

The reaction vessel 1 serves as a vessel to contain the analyte 2 (the analyte-reagent mixture), and a drive mechanism 3 is provided for moving the reaction vessel 1 horizontally and vertically based on a drive signal from the controller 12. The reaction vessel 1 is formed of electrically conductive material and connected electrically via a signal line 1a to a liquid-surface detector 13 of the liquid-surface detector unit 80 (described later).

The probe 4 is soaked into the analyte 2 contained in the reaction vessel 1 to suction the analyte 2. A drive mechanism 5 is provided for moving the probe 4 horizontally and vertically based on a drive signal from the controller 12. The probe 4 is formed of electrically conductive material also and connected electrically via signal lines 4a and 4b to the liquid-surface detector 13 of the liquid-surface detector unit 80

(described later). Note however that a switch 15, described later, is used to electrically connect or disconnect the signal line 4a to/from the signal line 4b.

The liquid-surface detector unit 80 includes the following components: the liquid-surface detector 13, the switch 15, and a power source 14. The liquid-surface detector 13 is designed to examine the electrical characteristics between the analyte 2 and the probe 4 obtained through the signal lines 1a, 4a, and 4b, thereby detecting the liquid surface level of the analyte 2 relative to the probe 4. The switch 15 is provided between the signal lines 4a and 4b to connect or disconnect the signal line 4a to/from the signal line 4b. The power source 14 is used to power the liquid-surface detector 13.

The switch 15 can either be in the closed position or the open position. When it is in the open position, the signal line 4a is electrically disconnected from the signal line 4b. When in the closed position, the switch 15 electrically connects the signal lines 4a and 4b.

Figure 2:
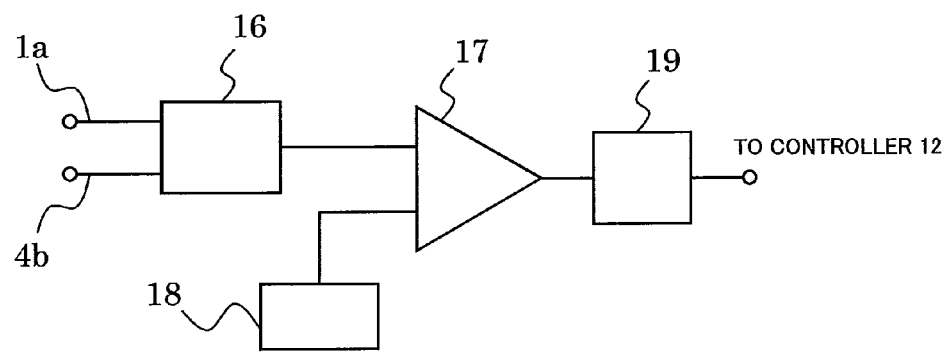
FIG. 2 is a schematic illustrating the configuration of the liquid-surface detector unit of the automatic analyzer.

The liquid-surface detector 13 of the liquid-surface detector unit 80 will now be described in detail with reference to FIG. 2. FIG. 2 is a schematic illustrating the configuration of the liquid-surface detector 13 of the liquid-surface detector unit 80.

As illustrated in FIG. 2, the liquid-surface detector 13 includes the following components: a value-change detector 16, a threshold storage unit 18, a comparator 17, and an output processor 19. The value-change detector 16 is designed to detect numerically how much the electrical characteristics between the reaction vessel 1 and the probe 4 have changed (examples of those electrical characteristics including capacitance and resistance) and then output the change quantity as a voltage signal. The threshold storage unit 18 is used to store a threshold value with which to judge whether the probe 4 has or has not touched the liquid surface of the analyte 2 or has or has not been soaked into the analyte 2. The comparator 17 is used to compare the voltage signal from the value-change detector 16 against the threshold value stored by the threshold storage unit 18 and then output the result as a liquid-surface detection signal. The output processor 19 converts this detection signal received from the comparator 17 into a given format and outputs the converted signal to the controller 12.

When the switch 15 is in the closed position, the value-change detector 16 detects numerically, through the signal lines 1a, 4a, and 4b, how much the electrical characteristics (e.g., capacitance or resistance) between the liquid surface of the analyte 2 within the reaction vessel 1 and the probe 4 have changed from reference values. The value-change detector 16 then converts the detected result into a voltage signal and outputs the signal to the comparator 17. As such reference values, a storage unit, not illustrated, stores in advance the electrical characteristics that are obtained when, for example, the probe 4 is about to approach the analyte 2. When the switch 15 is the open position, in contrast, there is no electrical connection between the signal lines 4a and 4b. Thus, when the switch 15 is in the open position, the value-change detector 16 detects neither the electrical characteristics between the liquid surface of the analyte 2 and the probe 4 nor their changes.

As stated, the comparator 17 compares the voltage signal from the value-change detector 16 against the threshold value stored by the threshold storage unit 18. Determining that the probe 4 has touched the liquid surface of the analyte 2 or has been soaked into the analyte 2, the comparator 17 outputs the comparison result as a liquid-surface detection signal to the output processor 19.

As above, the liquid-surface detector 13 detects the liquid surface level of the analyte 2 relative to the probe 4, by judging whether the probe 4 has or has not touched the liquid surface of the analyte 2 or has or has not been soaked into the analyte 2.

Refer to FIG. 1.

With reference again to FIG. 1, the transfer unit 70 includes the following components: a channel 7a, connecting the probe 4 and the analyzer unit 6, through which the analyte 2 is transferred from the probe 4 to the analyzer unit 6; a syringe 10; and a channel 7b for connecting the analyzer unit 6 and the syringe 10.

The syringe 10 includes the following components: a piston 11 that slides along the inner surface of the syringe 10 with a reciprocal motion; and a drive mechanism, not illustrated, for moving the piston 11 linearly based on a drive signal from the controller 12. Note that in the explanation that follows, the moving directions of the piston 11 in which the inner volume of the syringe 10 increases and decreases are referred to as the suction direction and the discharge direction, respectively. When the probe 4 is immersed in the analyte 2, moving the piston 11 in the suction direction causes the air inside the analyzer unit 6 to be drawn toward the syringe 10, that is, into the channel 7b, thus allowing the analyte 2 to be transferred from the probe 4 through the channel 7a to the analyzer unit 6. When the piston 11 is moved in the discharge direction, in contrast, the analyte 2 inside the analyzer unit 6 flows out of the probe 4 through the channel 7a.

The analyzer unit 6 performs analysis of the analyte 2 and is designed to measure, for example, the concentration of a particular type of ion in the analyte 2. This requires the use of two types of electrodes: one or more electrodes 8 each designed to detect a certain type of ion (only one electrode 8 shown in FIG. 1 for the sake of simplicity) and a reference electrode (not illustrated). By putting either one of the electrodes 8 and the reference electrode into the analyte 2 and thereby measuring the electric potential that arises between the two electrodes (i.e., measuring the potential difference), the concentration of a particular ion can be measured. After analyzing the analyte 2 with the use of the electrode(s) 8, the analyzer unit 6 outputs the analysis result (e.g., concentrations of particular ions) to the controller 12 via a signal line 8a.

The controller 12 governs the entire operation of the automatic analyzer, controlling the positions of the reaction vessel 1 and the probe 4, the operation of the liquid-surface detector 13, the operation of the switch 15 (open or closed), the position of the piston 11 inside the syringe 10, and so forth. The controller 12 also performs analysis of the analyte 2 using parameters received from an input device (not illustrated) or using software stored in a storage unit (not illustrated).

Described next with reference to FIGS. 3 through 9 is the analysis procedure according to the present embodiment.

Figure 3:
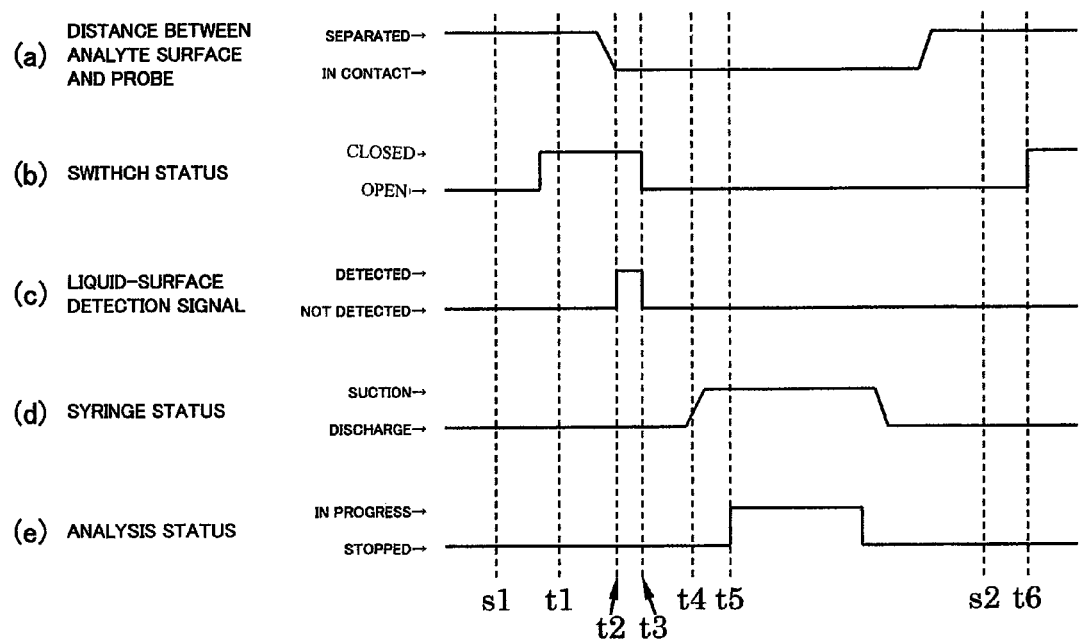
FIGS. 3 (a) through (e) are timing charts associated with the analysis procedure followed by the automatic analyzer on a component-by-component basis.

FIGS. 3 (a) through (e) are timing charts associated with the analysis procedure followed by the automatic analyzer. The horizontal axes of FIGS. 3 (a) to (e) represent time. The vertical axis of FIG. 3 (a) represents the distance from the liquid surface of the analyte 2 inside the reaction vessel 1 to the lower end of the probe 4. The vertical axis of FIG. 3 (b) indicates whether the switch 15 is in the open or closed position. The vertical axis of FIG. 3 (c) represents the status of a liquid-surface detection signal to be transmitted from the liquid-surface detector 13 to the controller 12. The vertical axis of FIG. 3 (d) indicates whether the probe 4 is suctioning the analyte 2 or not, that is, indicates the operational status of the syringe 10. The vertical axis of FIG. 3 (e) indicates the status of the analyzer unit 6.

FIGS. 4 to 9 are schematics illustrating the operational states of the automatic analyzer at times t1 to t6, respectively, of FIG. 3.

Figure 4:
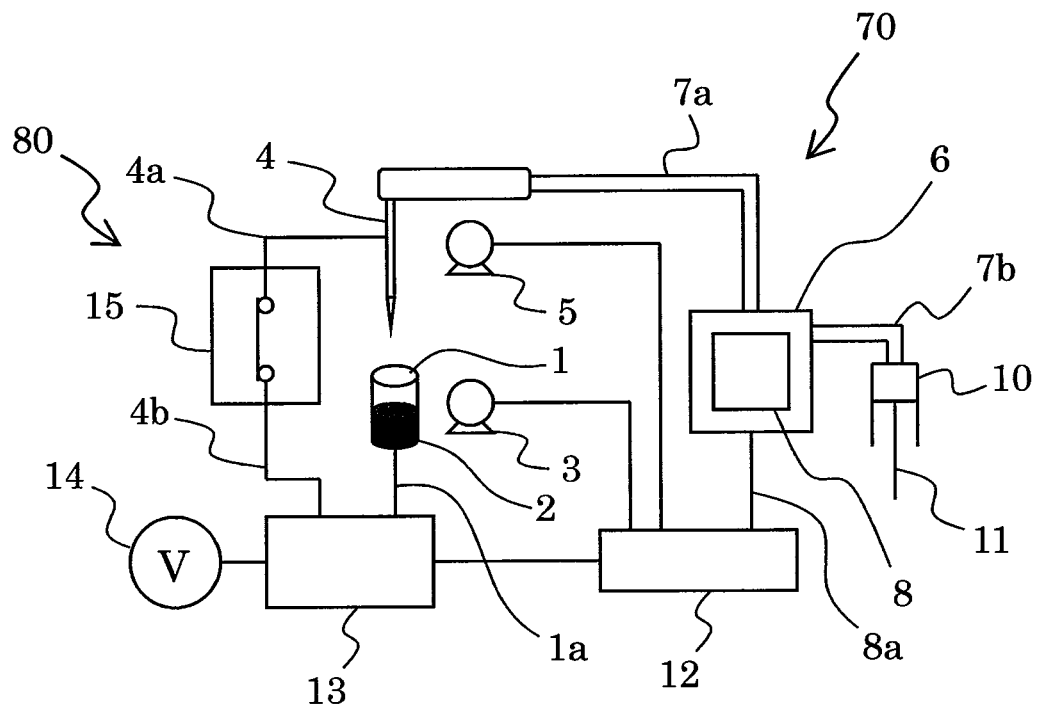
FIG. 4 is a schematic illustrating the status of the automatic analyzer at time t1 of FIG. 3.

To start an analysis, the switch 15 is first shifted from the open position to the closed position as illustrated in FIG. 3 (*b*), which takes place at time s1 from which one cycle of analysis begins. At time t1, then, the switch 15 is in the closed position, as depicted in FIG. 4.

Figure 5:
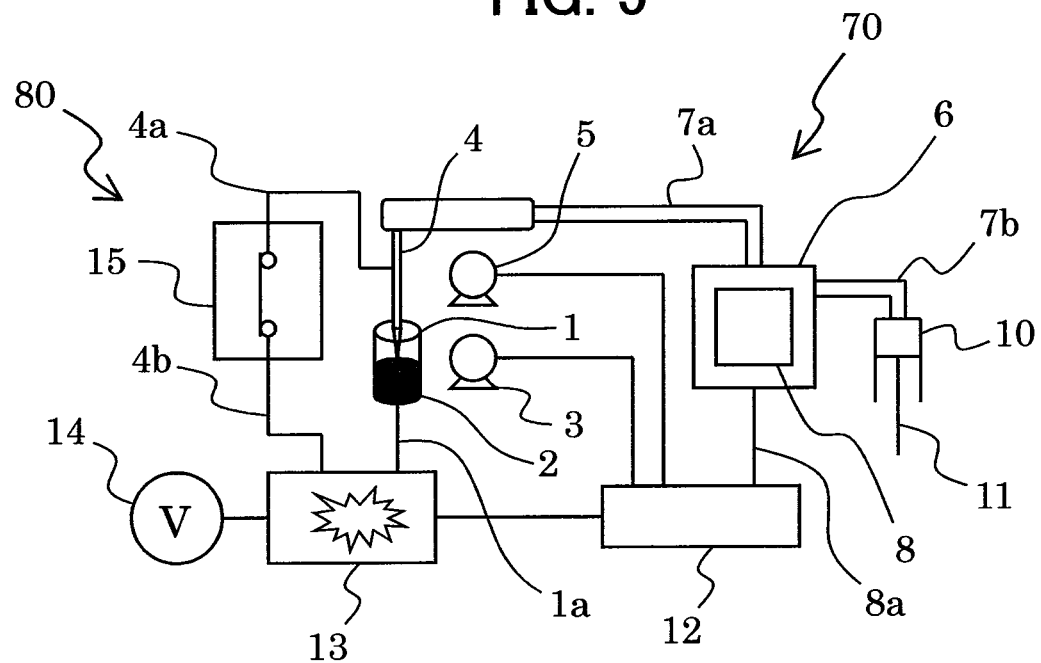
FIG. 5 is a schematic illustrating the status of the automatic analyzer at time t2 of FIG. 3.

Next, the probe 4 is drawn nearer to the liquid surface of the analyte 2. This movement of the probe 4 is stopped at time t2 when the liquid-surface detector 13 outputs a liquid-surface detection signal to the controller 12, as illustrated in FIG. 3 (*c*). As depicted in FIG. 5, the probe 4 is thus immersed in the analyte 2 at time t2.

Figure 6:
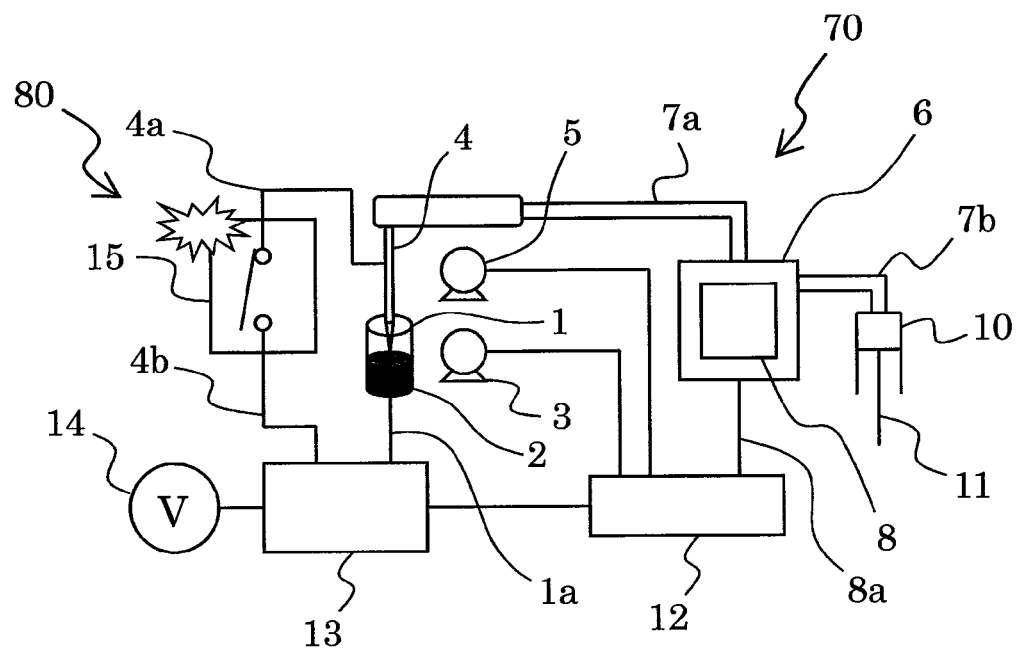
FIG. 6 is a schematic illustrating the status of the automatic analyzer at time t3 of FIG. 3.

The switch 15 is then shifted from the closed position to the open position at time t3, as illustrated in FIG. 3 (*b*). FIG. 6 depicts this state at time t3 where the switch 15 is in the open position.

Figure 7:
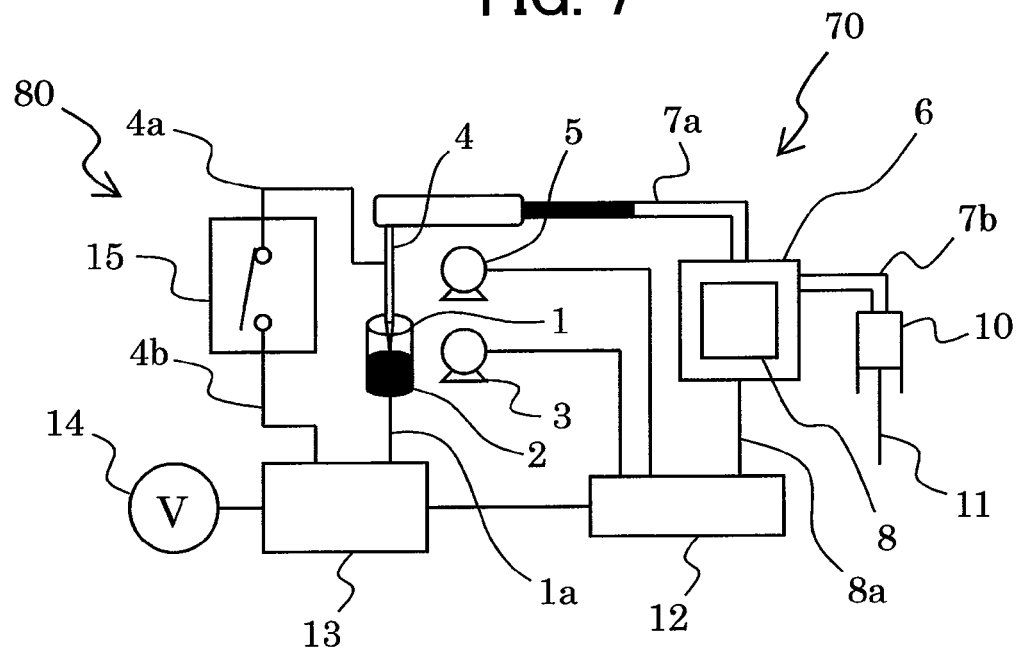
FIG. 7 is a schematic illustrating the status of the automatic analyzer at time t4 of FIG. 3.

Next, with the probe 4 being immersed in the analyte 2, the piston 11 of the syringe 10 is moved in the suction direction at time t4, as illustrated in FIG. 3 (*d*). FIG. 7 depicts this state at time t4 where the analyte 2 starts to be suctioned by the probe 4 and transferred through the channel 7*a* toward the analyzer unit 6.

Figure 8:
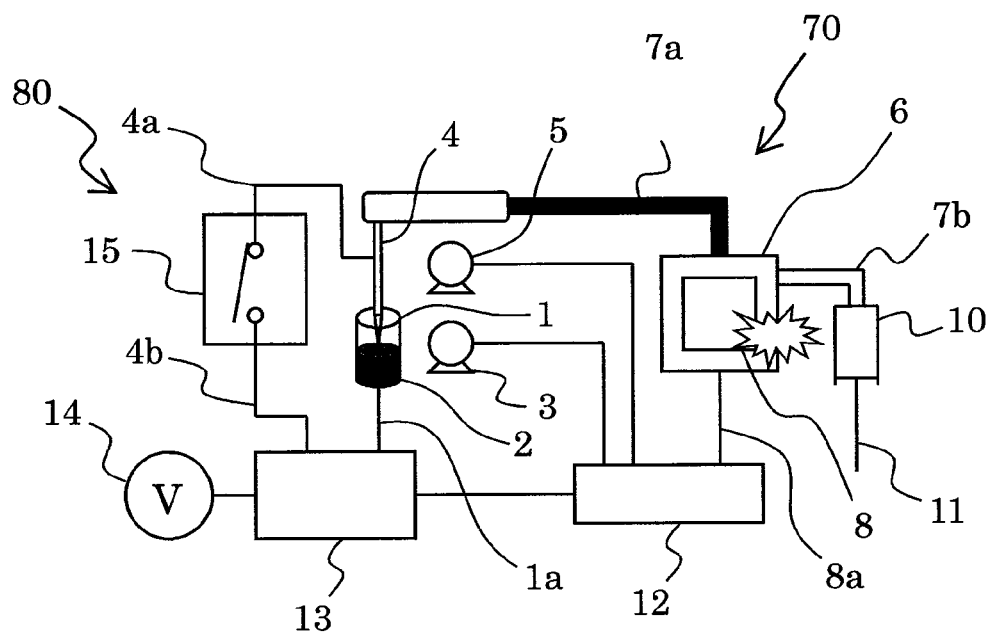
FIG. 8 is a schematic illustrating the status of the automatic analyzer at time t5 of FIG. 3.

After the analyte 2 reaches the analyzer unit 6, the analyzer unit 6 starts analysis, as illustrated in FIG. 3 (*e*) (also see FIG. 8). As is also illustrated in FIG. 3 (*e*), the analyzer unit 6 is caused to stop the analysis when it is complete. This is followed by the movement of the piston 11 of the syringe 10 in the discharge direction as illustrated in FIG. 3 (*d*), by the movement of the probe 4 away from the liquid surface of the analyte 2 as illustrated in FIG. 3 (*a*), and by a rinse of the probe 4, the transfer unit 70, and the analyzer unit 6 with the use of a rinse mechanism not illustrated.

Figure 9:
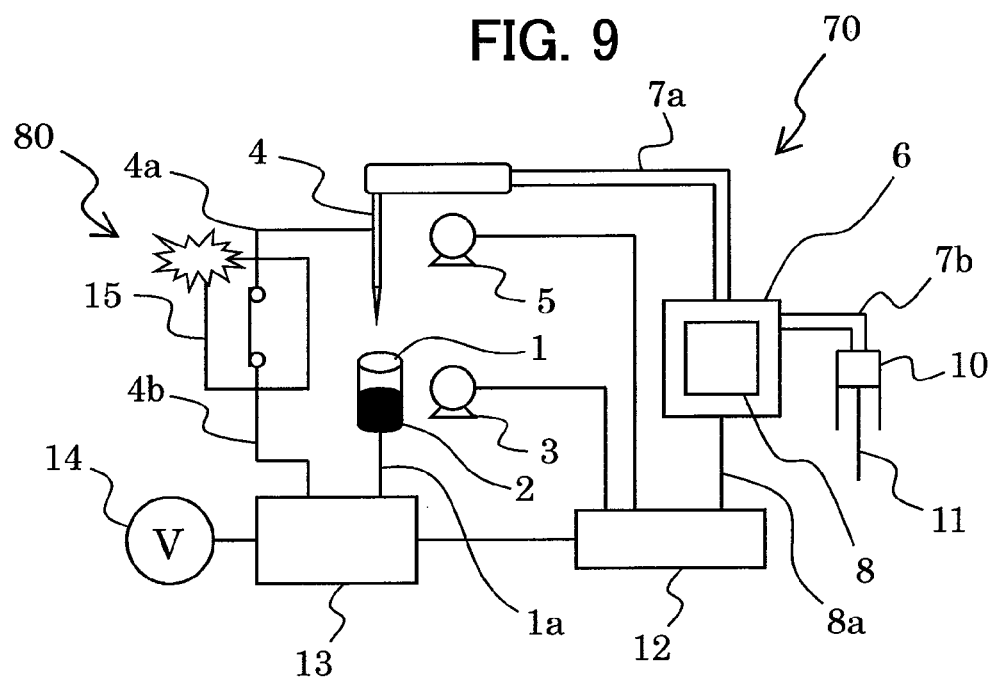
FIG. 9 is a schematic illustrating the status of the automatic analyzer at time t6 of FIG. 3.

Thereafter, as illustrated in FIG. 3 (*b*), the open position of the switch 15 which lasts up to time s2, or the start point of the next analysis cycle, is changed to the closed position at time t6 (also see FIG. 9).

The above-described analysis procedure that spans the period between time s1, the start point of an analysis cycle, and time s2, the start point of the next cycle, is repeated for as many analytes as are to be analyzed.

Advantages of the above automatic analyzer of the invention will now be described.

A known conventional liquid-surface detection technique for automatic analyzers involves the use of a probe both as an electrode and as an electrically active component. The probe is used for the detection of the capacitance between the probe and a grounded reaction vessel (i.e., the analyte therein, which is also grounded), and monitoring changes in the capacitance allows detection of the liquid surface level of the analyte relative to the probe. When an automatic analyzer employs such a technique, which may require a channel to be provided between its probe and analyzer unit for the transfer of an analyte, it may be difficult or impossible to obtain accurate analysis results. This is due to the possibility that electrical fluctuations (e.g., electric signals used for liquid-surface detection and associated electric noise) may adversely affect the analyzer unit through the probe and through the analyte flowing inside the channel. The present embodiment of the invention, in contrast, is provided with the switch 15 that changes the connection status of the signal lines 4*a* and 4*b* that connect the liquid-surface detector 13 to the probe 4, so that the signal line 4*a* can be disconnected electrically from the signal line 4*b* while the analyzer unit 6 is performing analysis of the analyte 2. This prevents analysis results from being adversely affected by electric signals used for liquid-surface detection and by electric noise, which leads to increased accuracy of automatic analysis.

Since the present embodiment prevents the above-described influences from affecting analysis results, it is possible, by adopting the present embodiment, for an automatic analyzer to have only one analyte transfer channel. It is so even when an analyte is to be transferred to the analyzer unit of the automatic analyzer by probe suctioning/discharging action as in the present embodiment, so as to avoid the influences of electric signals during liquid-surface detection. By an automatic analyzer having only one analyte transfer channel, there is no need to consider variations in the amounts of analytes to be transferred into its analyzer unit, which leads to increased analysis accuracy.

The above-described embodiment of the invention can be changed or modified in various forms without departing from the scope of the invention. For instance, while the embodiment is designed such that the switch 15 is provided as current-blocking means between the signal lines 4*a* and 4*b* that connect the probe 4 to the liquid-surface detector 13, the switch 15 can be placed at a different location as long as placing the switch 15 at such a location prevents the analyzer unit 6 from receiving electric signals used for liquid-surface detection and associated electric noise. One example of a possible location would be on the signal line 1*a* between the reaction vessel 1 and the liquid-surface detector 13. In this case, when the analyzer unit 6 performs an analysis with the probe 4 being soaked into the analyte 2, electric signals and noise that are generated from the liquid-surface detector 13 can be prevented from reaching the analyzer unit 6 through the reaction vessel 1 and through the analyte 2 therein.

The switch 15 can also be placed between the liquid-surface detector 13 and the power source 14. This arrangement can also stop the operation of the liquid-surface detector 13; thus, it is possible to prevent electric signals and noise, which have adverse effects on the analyzer unit 6, from being generated from their direct source.

It is also possible to place, as analyte-blocking means, a channel-switch valve (or a shutoff valve) on the channel 7*a* that connects the probe 4 to the analyzer unit 6. This prevents electric signals and noise from being transmitted to the analyzer unit 6 through the analyte 2 flowing inside the channel 7*a*.

Note also that the materials of the reaction vessel 1 and the probe 4 of the present embodiment are both electrically conductive, but not limited thereto. For example, an electrode can be attached to each portion of the reaction vessel 1 and the probe 4 that is to touch the analyte 2 (or an electrode can be attached to such an analyte-touching portion either of the reaction vessel 1 or of the probe 4), so that an electrical connection can be established between the electrode(s) and the liquid-surface detector 13.

Note further that while the present embodiment employs the switch 15 as current-blocking means, the switch 15 can be replaced by a transistor to serve the same function.

Furthermore, while the current-blocking means, or the switch 15, serves the function of severing the electrical connection between the signal lines 4*a* and 4*b*, these signal lines can instead be grounded or have a pull-up configuration in which a pull-up resistor is provided on the side of a given power source, depending on the intended use or on the configuration of the liquid-surface detector 13.

As stated above, the analyzer unit 6 is designed to measure inter-electrode potential differences with the use of the electrodes 8 and the like, thereby measuring ion concentrations of the analyte 2. However, the analyte 2 can instead be analyzed by applying voltage or the like between those electrodes. This requires detection of the resultant luminescence or luminescent colors of the analyte 2 with the use of a certain detector. In this case, electric signals and noise can be prevented from affecting the voltage applied to the electrodes 8 and the like.

DESCRIPTION OF THE REFERENCE NUMERALS

1: Reaction vessel
1a: Signal line
2: Analyte (analyte-reagent mixture)
3: Drive mechanism
4: Probe
4a, 4b: Signal line
5: Drive mechanism
6: Analyzer unit
7a, 7b: Channel
8: Electrode
8a: Signal line
10: Syringe
11: Piston
12: Controller
13: liquid-surface detector
14: Power source
15: Switch
16: Value-change detector
17: Comparator
18: Threshold storage unit
19: Output processor
70: Transfer unit
80: Liquid-surface detector unit

The invention claimed is:

1. An automatic analyzer comprising:
a reaction vessel in which an analyte is caused to react with a reagent;
a probe for suctioning the reacted analyte from the reaction vessel;
an analyzer unit for analyzing the reacted analyte;
a transfer channel for transferring the reacted analyte suctioned by the probe to the analyzer unit;
a liquid surface detector, connected to the probe and the reaction vessel via a signal line, for detecting electrical characteristics between the reaction vessel and the probe;
a physical switch disposed on the signal line connecting the liquid surface detector to the probe to prevent electrical fluctuations that arise from the liquid surface detector from reaching the analyzer unit; and
a processor programmed to open the physical switch to prevent electrical fluctuations arising from the liquid surface detector from reaching the analyzer unit while the analyzer unit is analyzing the reacted analyte.

2. The automatic analyzer of claim 1 wherein the physical switch is configured to sever an electrical connection of the signal line connecting the liquid surface detector to the probe.

* * * * *